(12) United States Patent
Sakamoto

(10) Patent No.: US 11,672,973 B2
(45) Date of Patent: *Jun. 13, 2023

(54) DEFIBRILLATION CATHETER SYSTEM, DEFIBRILLATION POWER SUPPLY DEVICE AND METHOD FOR CONTROLLING DEFIBRILLATION POWER SUPPLY DEVICE

(71) Applicant: KANEKA CORPORATION, Osaka (JP)

(72) Inventor: Shinichiro Sakamoto, Settsu (JP)

(73) Assignee: KANEKA CORPORATION, Osaka (JP)

(*) Notice: Subject to any disclaimer, the term of this patent is extended or adjusted under 35 U.S.C. 154(b) by 169 days.

This patent is subject to a terminal disclaimer.

(21) Appl. No.: 16/987,052

(22) Filed: Aug. 6, 2020

(65) Prior Publication Data
US 2020/0360686 A1 Nov. 19, 2020

Related U.S. Application Data

(63) Continuation of application No. PCT/JP2019/002978, filed on Jan. 29, 2019.

(30) Foreign Application Priority Data

Feb. 7, 2018 (JP) .............................. JP2018-020529

(51) Int. Cl.
*A61N 1/39* (2006.01)
*A61N 1/05* (2006.01)

(52) U.S. Cl.
CPC .......... *A61N 1/0563* (2013.01); *A61N 1/3906* (2013.01); *A61N 1/3925* (2013.01); *A61N 1/3981* (2013.01)

(58) Field of Classification Search
CPC ... A61N 1/0563; A61N 1/3906; A61N 1/3925
See application file for complete search history.

(56) References Cited

U.S. PATENT DOCUMENTS 4,077,413 A * 3/1978 Partridge ............. A61N 1/3904
D24/167
5,285,779 A * 2/1994 Cameron ............. A61N 1/3925
320/166

(Continued)

FOREIGN PATENT DOCUMENTS

JP 2010-220778 A 10/2010
JP 2017-176349 A 10/2017

OTHER PUBLICATIONS

International Search Report for PCT/JP2019/002978 dated Apr. 9, 2019.

*Primary Examiner* — Eric D. Bertram
(74) *Attorney, Agent, or Firm* — Birch, Stewart, Kolasch & Birch, LLP

(57) ABSTRACT

Provided are a defibrillation catheter system, a defibrillation power supply device, and a method for controlling the device during observation of intracardiac potential and defibrillation. A defibrillation catheter system 1 includes a catheter 20; a power supply part 6 connected to the catheter 20; an electrocardiograph 40 measuring an intracardiac potential; a first electrode 21 and a second electrode 22 provided on the catheter; and a changeover part 7 connected to the power supply part 6, the changeover part 7 switching between a first mode for measuring the intracardiac potential and a second mode for applying the voltage while the intracardiac potential is measured, wherein the first electrode 21 and the second electrode 22 are connected to the power supply part 6 through the changeover part 7, and the first electrode 21 and the second electrode 22 are connected to the electrocardiograph 40.

11 Claims, 6 Drawing Sheets

(56) References Cited

U.S. PATENT DOCUMENTS

| 5,522,850 | A | | 6/1996 | Yomtov et al. | |
|---|---|---|---|---|---|
| 5,757,167 | A | * | 5/1998 | Arora | G05F 1/59 |
| | | | | | 323/224 |
| 6,016,446 | A | * | 1/2000 | Belalcazar | A61N 1/3704 |
| | | | | | 607/9 |
| 2009/0036943 | A1 | * | 2/2009 | Signoff | A61N 1/378 |
| | | | | | 607/36 |
| 2010/0114215 | A1 | * | 5/2010 | Burnes | A61N 1/39624 |
| | | | | | 607/34 |
| 2011/0319948 | A1 | * | 12/2011 | Onodera | A61N 1/0563 |
| | | | | | 607/5 |

* cited by examiner

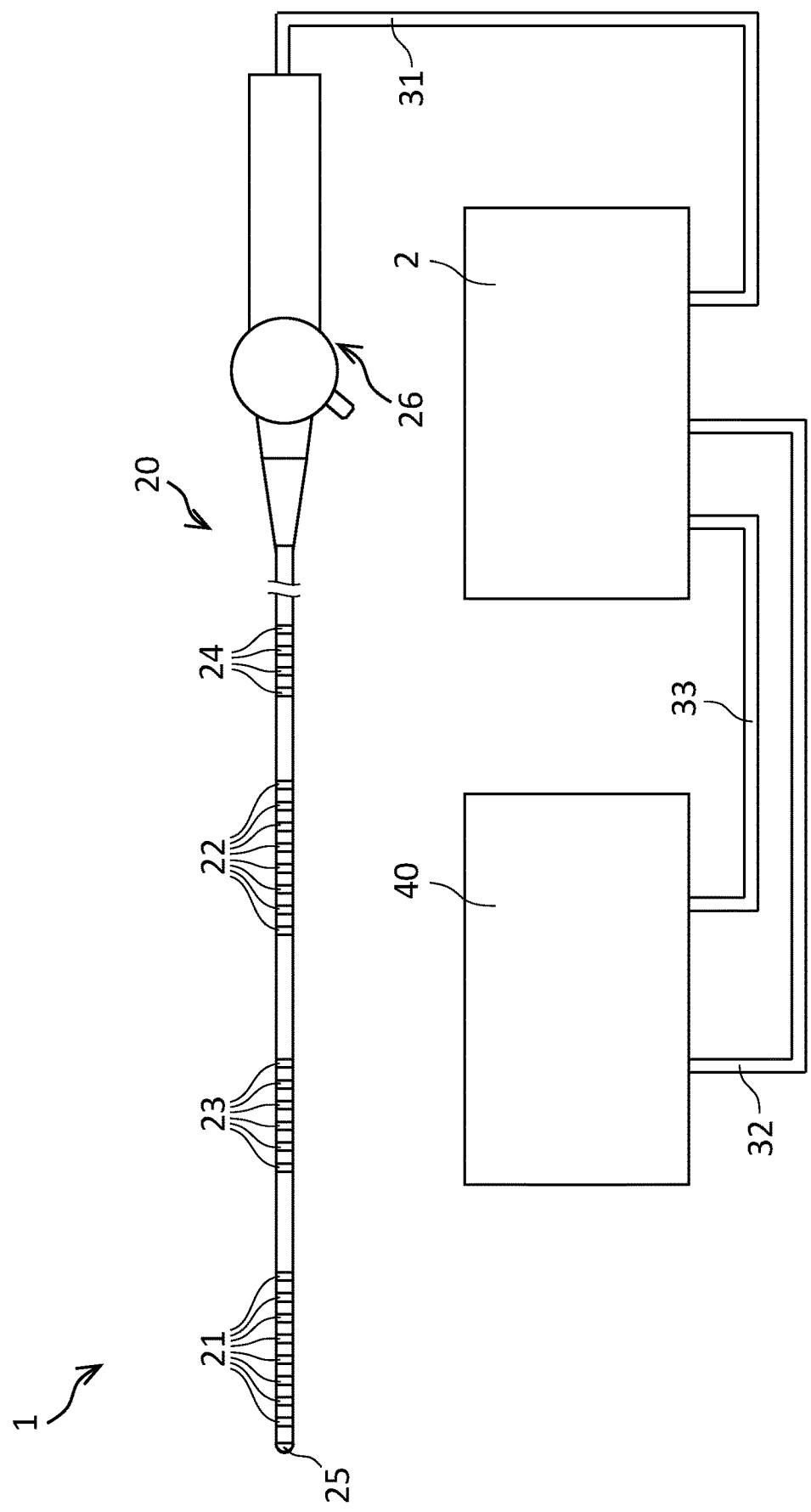
[Fig. 1]

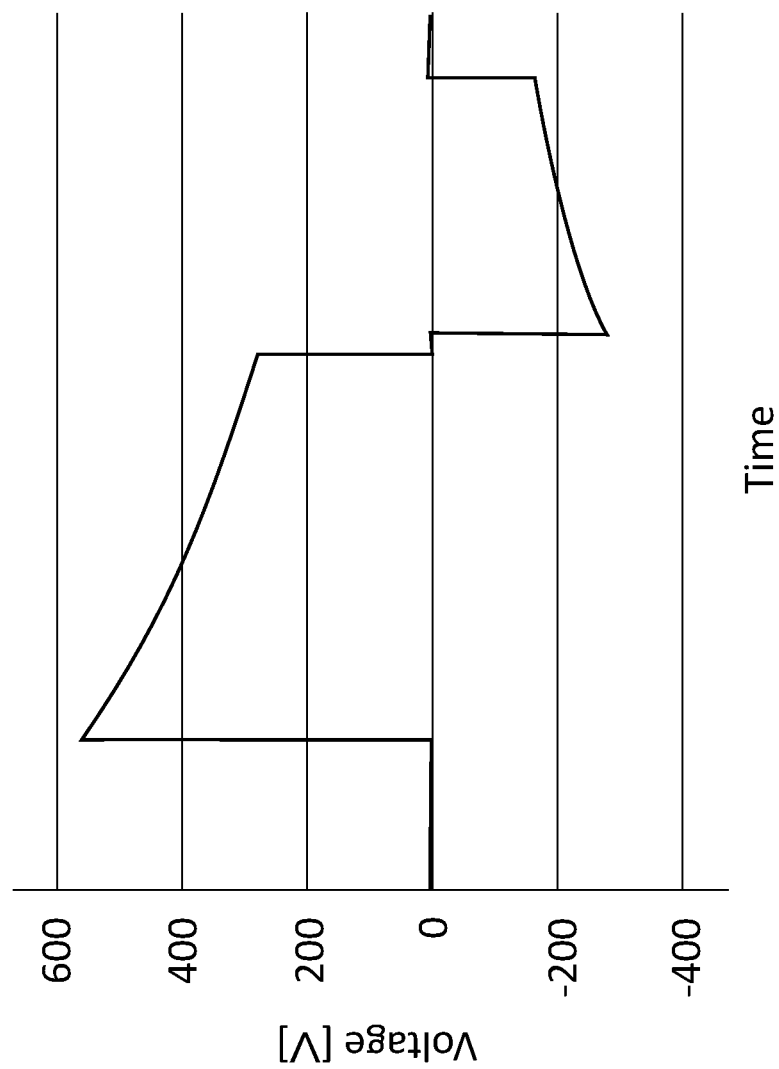
[Fig. 2]

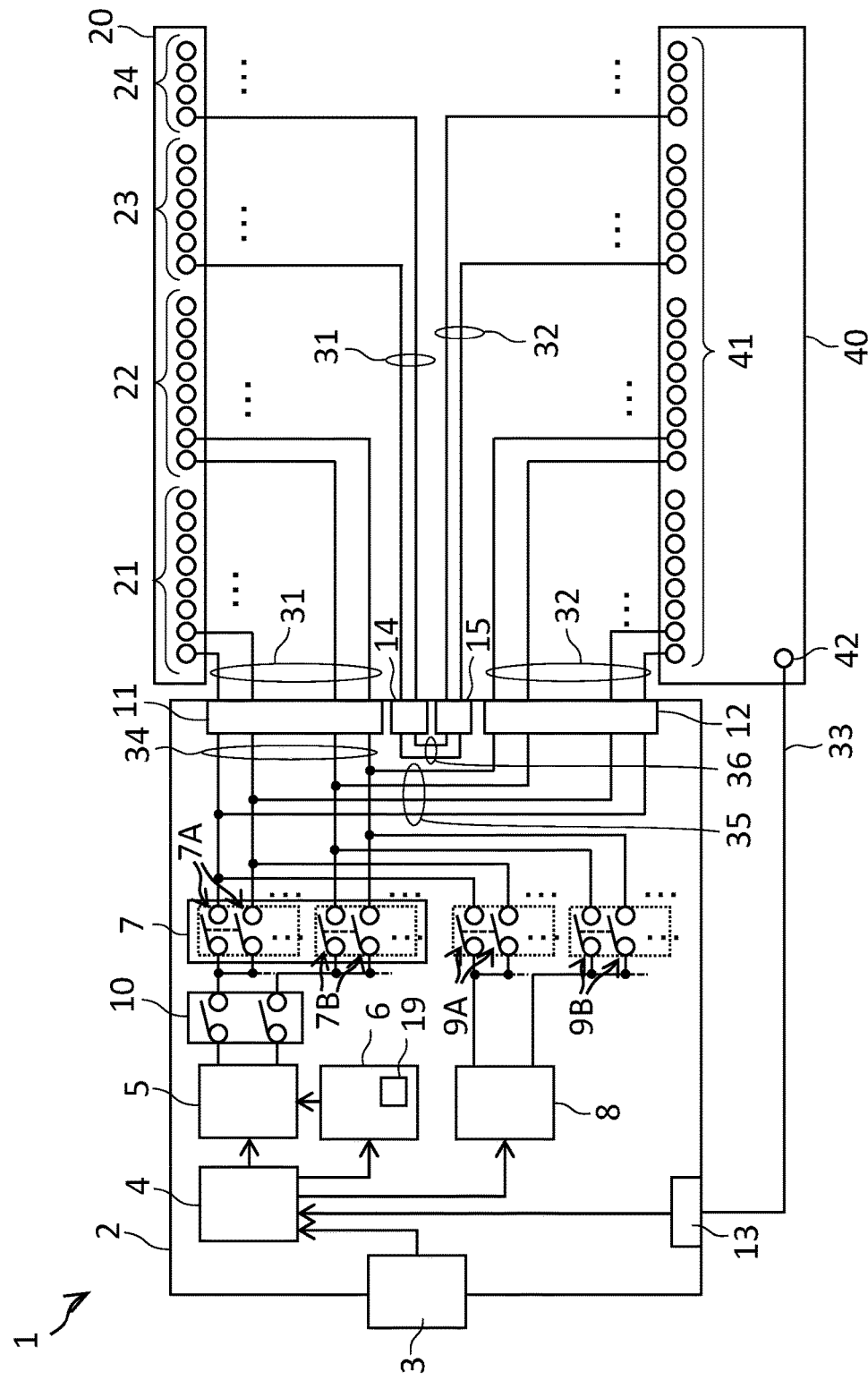
[Fig. 3]

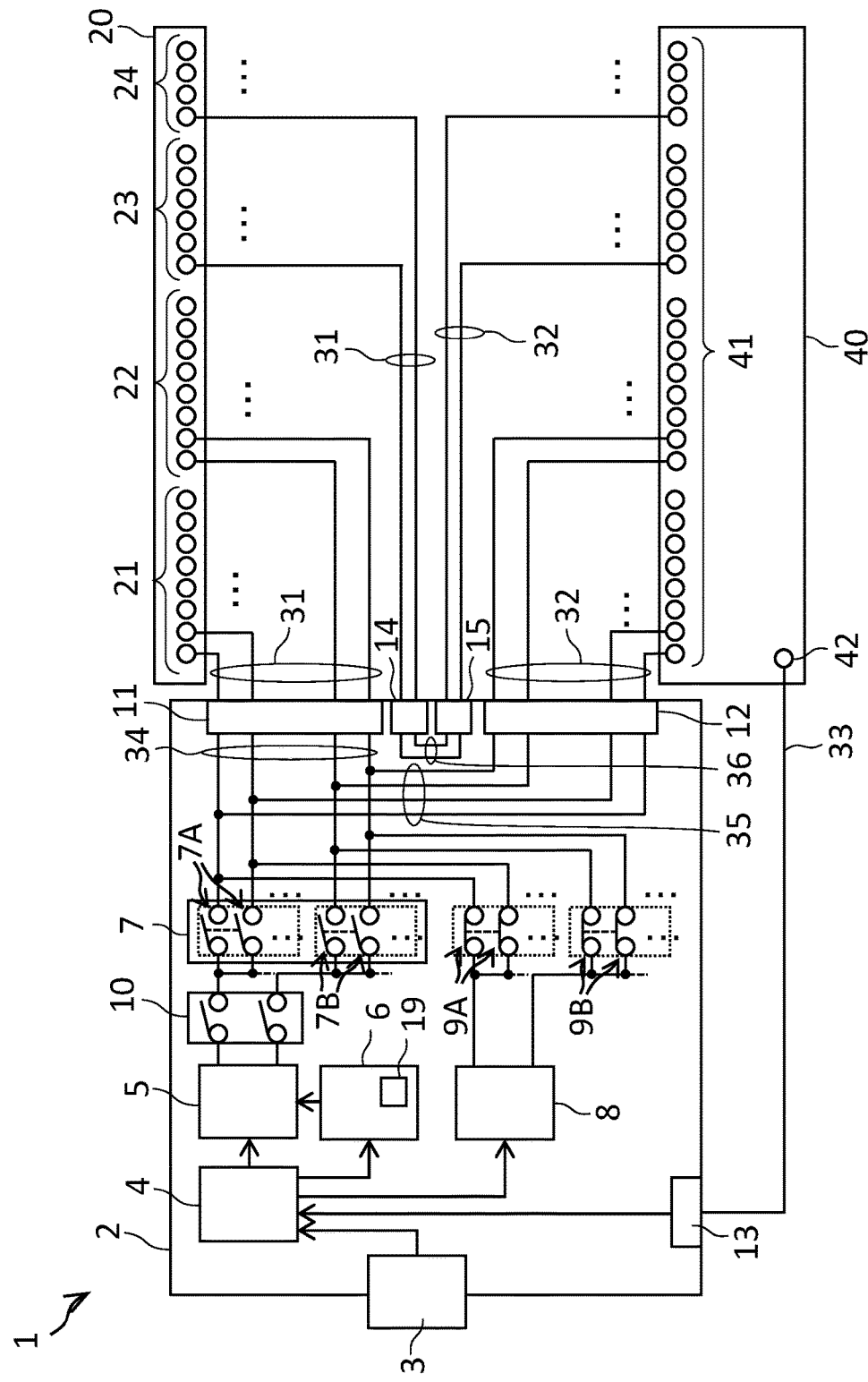
[Fig. 4]

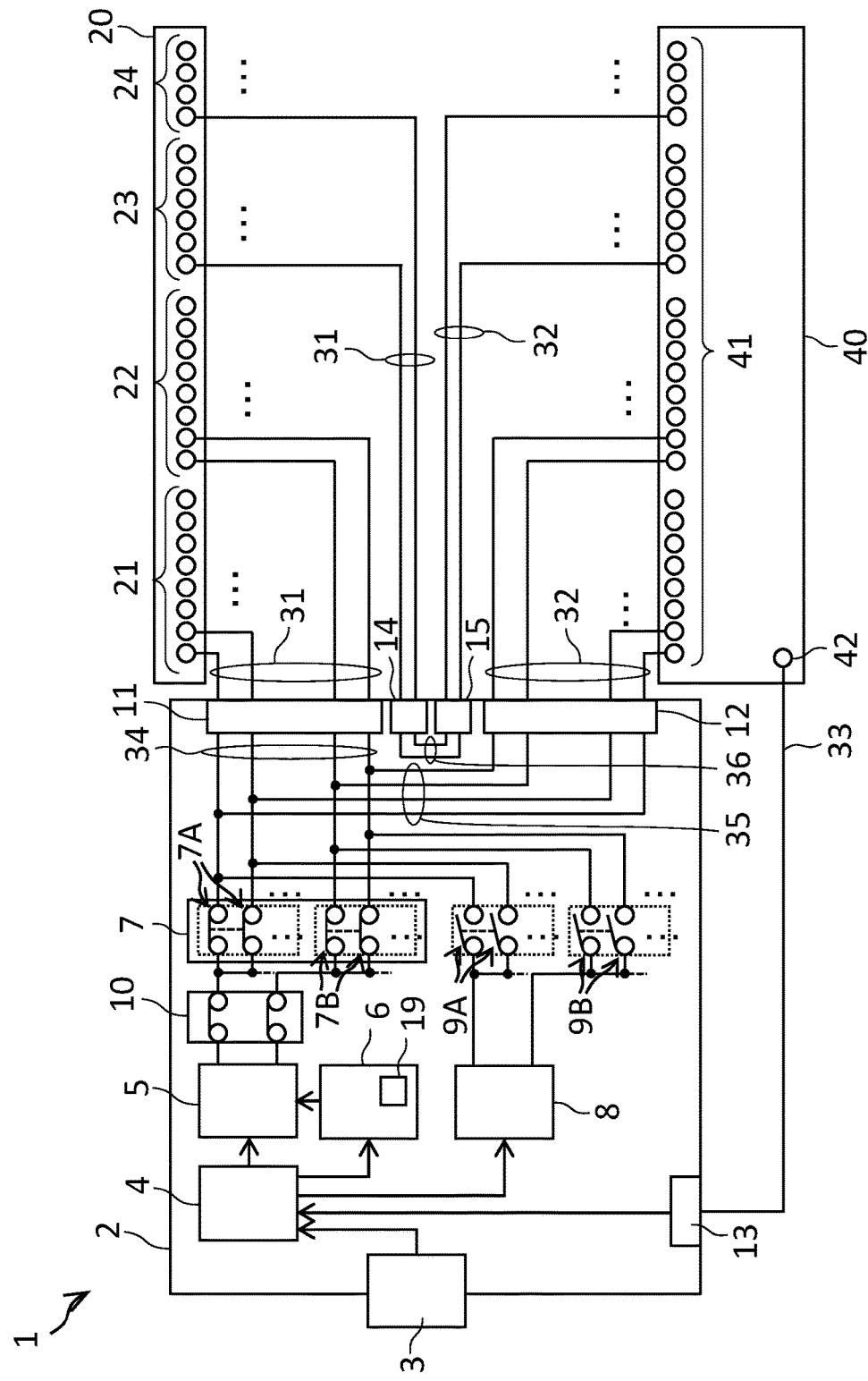
[Fig. 5]

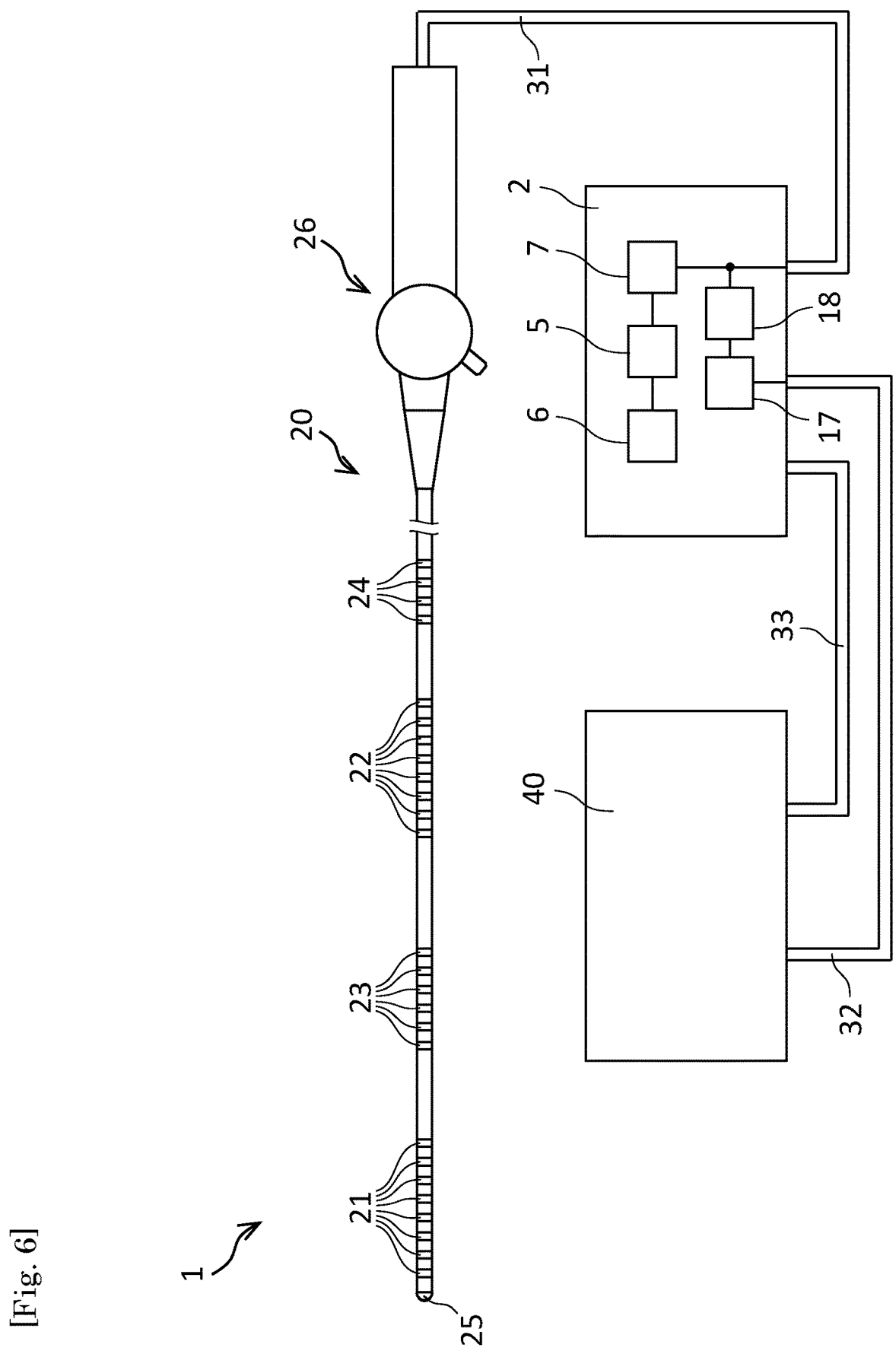
[Fig. 6]

DEFIBRILLATION CATHETER SYSTEM, DEFIBRILLATION POWER SUPPLY DEVICE AND METHOD FOR CONTROLLING DEFIBRILLATION POWER SUPPLY DEVICE

CROSS REFERENCE TO RELATED APPLICATIONS

This application is a Continuation of PCT International Application No. PCT/JP2019/002978, filed on Jan. 29, 2019, which claims priority under 35 U.S.C. 119(a) to Patent Application No. 2018-020529, filed in Japan on Feb. 7, 2018, all of which are hereby expressly incorporated by reference into the present application.

TECHNICAL FIELD

The present invention relates to a catheter system for performing defibrillation, a power supply device for, for example, generating a voltage waveform to be applied during defibrillation and selecting an electrode to which a voltage is applied, and a method for controlling the device.

BACKGROUND ART

In the treatment of arrhythmia such as atrial fibrillation or ventricular fibrillation, defibrillation is performed to restore the heart rhythm to normal by applying electrical stimulation. For the defibrillation, an automated external defibrillator (AED), an implantable cardioverter defibrillator (ICD), a defibrillation paddle system, and a defibrillation catheter system are used. In particular, the defibrillation catheter system can measure an intracardiac potential using an electrode provided on the surface of the catheter, while directly applying electrical stimulation to the heart through the electrode. In addition, the defibrillation catheter system is advantageous in that it can use a voltage waveform with lower energy than the external defibrillator, by which the burden on a patient is reduced. The defibrillation catheter system is also advantageous in that it can also be used during ablation and cardiac catheterization for diagnosis of arrhythmia.

In the treatment of atrial fibrillation, it is necessary to apply a voltage during an absolute refractory period so that the ventricular muscles do not respond. If stimulation is applied during periods other than the absolute refractory period, ventricular muscles may respond to cause ventricular fibrillation. Therefore, in the defibrillation catheter system, it is necessary to apply the voltage in synchronization with the R wave.

As an example of such a defibrillation catheter system, Patent Document 1 discloses a catheter system including a defibrillation catheter, a power supply device for applying a DC voltage to electrodes of the catheter, and an electrocardiograph. This system uses a changeover switch with one circuit and two contacts to switch between defibrillation and measurement of intracardiac potential. Therefore, this system cannot unfortunately acquire the intracardiac potential during charging of energy to be delivered for defibrillation and during defibrillation.

In view of this, a system capable of measuring an intracardiac potential during execution of intracardiac defibrillation has been developed. For example, Patent Document 2 discloses, during intracardiac defibrillation, connecting some (RA electrode and CS electrode) of electrodes of an electrode catheter to an electrocardiograph through a protective resistance, instead of completely cutting off the connection between the electrocardiograph and the electrode catheter.

RELATED ART DOCUMENTS

Patent Documents

Patent Document 1: JP2010-220778A
Patent Document 2: JP2017-176349A

SUMMARY OF THE INVENTION

Technical Problem

In the intracardiac defibrillation system disclosed in Patent Document 2, during intracardiac defibrillation in which an on-off switch is in off state, an intracardiac potential signal is transferred to the electrocardiograph through the protective resistance having a relatively large resistance value, so that an intracardiac electrographic waveform displayed in the electrocardiograph is damped more than that during intracardiac electrocardiographic measurement where the on-off switch is in on state. In addition, during intracardiac defibrillation, an electrode catheter short switch is in a short state, so that one measured potential is obtained by averaging the potentials of the eight RA electrodes, and one measured potential is obtained by averaging the potentials of the eight CS electrodes. Therefore, the electrocardiogram of the RA electrodes and the CS electrodes has a rounding waveform as compared with that during the intracardiac electrocardiographic measurement, and the intracardiac potential cannot independently be acquired at each electrode. Furthermore, independent on-off switches are each required for eight CS electrodes and eight RA electrodes, which may increase the circuit scale and require complex control. In view of this, an object of the present invention is to provide a defibrillation catheter system, a defibrillation power supply device, and a method for controlling the device that enable observation of intracardiac potential even during defibrillation in the same manner as during intracardiac electrocardiographic measurement, and that can be easily controlled.

Solutions to the Problems

The gist of a defibrillation catheter system according to the present invention that can overcome the above problems is as follows. A defibrillation catheter system includes a catheter extending in a longitudinal direction; a power supply part for generating a voltage to be applied to the catheter, the power supply part connected to the catheter; an electrocardiograph for measuring an intracardiac potential; a first electrode provided on a distal side of the catheter; a second electrode provided on the distal side of the catheter and disposed closer to a proximal side than the first electrode; and a changeover part connected to the power supply part, the changeover part switching between a first mode for measuring the intracardiac potential and a second mode for applying the voltage to the catheter while the intracardiac potential is measured. The first electrode and the second electrode are connected to the power supply part through the changeover part, and the first electrode and the second electrode are connected to the electrocardiograph without a switching part. As described above, in the defibrillation catheter system according to the present invention, the first electrode and the second electrode are connected to the electrocardiograph without a switching part, whereby local potentials at the respective electrodes can be measured even during defibrillation.

In the defibrillation catheter system, the changeover part preferably has first switches connected in parallel with each other and second switches connected in parallel with each other, the catheter preferably has a plurality of the first electrodes and a plurality of the second electrodes, each of the first electrodes is connected to the power supply part through a corresponding one of the first switches, and each of the second electrodes is connected to the power supply part through a corresponding one of the second switches.

In the defibrillation catheter system, the first switches and the second switches are preferably of a multi-pole single-throw switch.

The defibrillation catheter system may include an electrode selection switch selecting from the first and second electrodes at least one electrode to which a voltage is applied, the electrode selection switch being connected to the power supply part.

The defibrillation catheter system preferably further includes a resistance of 200Ω or less, the resistance being provided between the power supply part and the electrocardiograph.

The defibrillation catheter system may further include an overvoltage protection circuit for protecting the electrocardiograph from an overvoltage, the overvoltage protection circuit being provided between the power supply part and the electrocardiograph.

The defibrillation catheter system preferably further includes an impedance measuring circuit for measuring an impedance between the first electrode and the second electrode, the impedance measuring circuit being connected between the first electrode and the second electrode. The first electrode is preferably connected to the impedance measuring circuit through a third switch, and the second electrode is preferably connected to the impedance measuring circuit through a fourth switch.

The defibrillation catheter system preferably further includes a third electrode for measuring the intracardiac potential, the third electrode provided between the first electrode and the second electrode in the longitudinal direction of the catheter.

The defibrillation catheter system preferably further includes a fourth electrode for measuring the intracardiac potential, the fourth electrode provided closer to the proximal side than the second electrode in the longitudinal direction of the catheter.

The defibrillation catheter system preferably includes, as the power supply part, at least a first power supply part and a second power supply part, and as the changeover part, at least a first changeover part and a second changeover part. The catheter preferably has, as the first electrode, at least a 1-1 electrode and a 1-2 electrode, and as the second electrode, at least a 2-1 electrode and a 2-2 electrode, the first power supply part is preferably connected to the first changeover part, the second power supply part is preferably connected to the second changeover part, the 1-1 electrode and the 2-1 electrode are preferably connected to the first power supply part through the first changeover part, the 1-2 electrode and the 2-2 electrode are preferably connected to the second power supply part through the second changeover part, and the 1-1 electrode, the 1-2 electrode, the 2-1 electrode, and the 2-2 electrode are preferably connected to the electrocardiograph without a switching part.

The present invention also includes a defibrillation power supply device to be connected to an electrocardiograph and a catheter having electrodes. The defibrillation power supply device according to the present invention includes a first connecting part to be connected to electrodes provided on a distal side of the catheter; a second connecting part to be connected to the electrocardiograph; a power supply part for generating the voltage to be applied; and a changeover part connected to the power supply part, the changeover part switching between a first mode for measuring an intracardiac potential by the electrocardiograph and a second mode for applying the voltage to the catheter while the intracardiac potential is measured. The first connecting part is connected to the power supply part through the changeover part, and the first connecting part is connected to the second connecting part without a switching part. In the defibrillation power supply device according to the present invention, the first connecting part is connected to the second connecting part without a switching part, whereby local potentials at the respective electrodes can be measured even during defibrillation.

The present invention also includes a method for controlling a defibrillation power supply device that is connected to an electrocardiograph and a catheter having an electrode, and that generates a voltage to be applied. The defibrillation power supply device includes a capacitor and a changeover part, the changeover part switching between a first mode for measuring an intracardiac potential by the electrocardiograph and a second mode for applying the voltage to the catheter while the intracardiac potential is measured by the electrocardiograph. The method includes charging the capacitor with the voltage to be applied while the intracardiac potential is measured by the electrocardiograph when the changeover part is in the first mode. According to the method for controlling, an intracardiac potential having no rounding waveform can be measured independently using each electrode even while the capacitor is being charged.

Advantageous Effects of the Invention

According to the defibrillation catheter system and the defibrillation power supply device of the present invention, the intracardiac potential at each electrode can be measured even during defibrillation. Further, according to the method for controlling the defibrillation power supply device of the present invention, an intracardiac potential having no rounding waveform can be measured independently using each electrode even while the capacitor is being charged.

BRIEF DESCRIPTION OF DRAWINGS

FIG. 1 is a schematic diagram showing a configuration of a defibrillation catheter system according to an embodiment of the present invention.

FIG. 2 is a diagram showing an example of a waveform to be applied by a defibrillation catheter system according to the embodiment of the present invention.

FIG. 3 is a block diagram showing a state in a first mode of a defibrillation catheter system according to the embodiment of the present invention.

FIG. 4 is a block diagram showing a measurement state of impedance of a defibrillation catheter system according to the embodiment of the present invention.

FIG. 5 is a block diagram showing a state in a second mode of a defibrillation catheter system according to the embodiment of the present invention.

FIG. 6 is a schematic diagram showing another configuration of a defibrillation catheter system according to the embodiment of the present invention.

DESCRIPTION OF EMBODIMENTS

The present invention will be specifically explained below based on the following embodiments, however, the present invention is not restricted by the embodiments described below of course, and can be certainly put into practice after appropriate modifications within in a range meeting the gist of the above and the below, all of which are included in the technical scope of the present invention. In the drawings, hatching, a reference sign for a member may be omitted for convenience, and in such a case, the description and other drawings should be referred to. In addition, sizes of various members in the drawings may differ from the actual sizes thereof, since priority is given to understanding the features of the present invention.

A defibrillation catheter system according to the present invention includes a catheter extending in a longitudinal direction; a power supply part for generating a voltage to be applied to the catheter, the power supply part connected to the catheter; an electrocardiograph for measuring an intracardiac potential; a first electrode provided on a distal side of the catheter; a second electrode provided on the distal side of the catheter and disposed closer to a proximal side than the first electrode; and a changeover part connected to the power supply part, the changeover part switching between a first mode for measuring the intracardiac potential and a second mode for applying the voltage to the catheter while the intracardiac potential is measured. The first electrode and the second electrode are connected to the power supply part through the changeover part, and the first electrode and the second electrode are connected to the electrocardiograph without a switching part. As described above, in the defibrillation catheter system according to the present invention, the first electrode and the second electrode are connected to the electrocardiograph without a switching part, whereby local potentials at the respective electrodes can be measured even during defibrillation.

A defibrillation catheter system 1 and a defibrillation power supply device 2 according to the present invention will be described with reference to FIGS. 1 to 6. FIG. 1 is a schematic diagram showing a configuration of the defibrillation catheter system 1 according to an embodiment of the present invention, and FIG. 2 is a diagram showing an example of a waveform to be applied by the defibrillation catheter system 1 according to the embodiment of the present invention. FIGS. 3 to 5 are block diagrams of the defibrillation catheter system 1 according to the embodiment of the present invention. FIG. 6 is a schematic diagram showing another configuration of a defibrillation catheter system according to the embodiment of the present invention. FIG. 3 shows a state in a first mode for measuring an intracardiac potential, FIG. 4 shows a measurement state of impedance, and FIG. 5 shows a state in a second mode for applying a voltage while the intracardiac potential is measured. Here, a proximal side of a catheter 20 refers to a direction of a hand side of a user (operator) against an extending direction of the catheter 20, and the distal side refers to an opposite direction to the proximal side (that is, a direction of a treatment target side). In addition, a direction from the proximal side to the distal side of the catheter 20 is referred to as a longitudinal direction.

First Embodiment

As shown in FIG. 1, the catheter 20 extends in a longitudinal direction, and is provided with a first electrode 21 on a distal side thereof and a second electrode 22 disposed closer to a proximal side than the first electrode 21. When the catheter 20 is inserted into a cardiac cavity, and the first electrode 21 and the second electrode 22 are brought into contact with the inner surface of the atrium, ventricle, or blood vessel, the intracardiac potential can be measured by the first electrode 21 and the second electrode 22. Moreover, the heart can be stimulated by applying a voltage to the first electrode 21 and the second electrode 22. Specifically, a voltage is applied such that a current flows from the first electrode 21 to the second electrode 22 via a living body or from the second electrode 22 to the first electrode 21 via the living body.

Examples of the catheter 20 include a resin tube formed in a tubular shape. The resin tube can be manufactured by, for example, extrusion molding. Examples of the resin constituting the catheter 20 include polyamide resin, polyester resin, polyurethane resin, polyolefin resin, fluorine resin, vinyl chloride resin, silicone resin, and natural rubber. These materials may be used alone, or two or more of them may be used in combination. Among them, polyamide resin, polyester resin, polyurethane resin, polyolefin resin, and fluorine resin are preferably used.

The catheter 20 may have a single-layer structure or a multi-layer structure. The catheter 20 may be configured such that a part in the longitudinal direction or in the circumferential direction is composed of a single layer, and another part is composed of multiple layers. The catheter 20 may also have one or more lumens.

It is preferable that, when the catheter 20 is inserted into the cardiac cavity, the first electrode 21 be placed in a position corresponding to the coronary sinus, and the second electrode 22 be placed in a position corresponding to the right atrium. Due to the first electrode 21 and the second electrode 22 being placed as described above, atrial fibrillation can be terminated efficiently.

To the first electrode 21 and the second electrode 22, DC voltages of different polarities are preferably applied. For example, when a biphasic DC voltage as shown in FIG. 2 is applied, fibrillation can be terminated with a small amount of energy.

The catheter 20 may have first electrodes 21 and second electrodes 22. If multiple electrodes are provided, the intracardiac potential can be acquired at various positions. For example, the intracardiac potential between the adjacent first electrodes 21 can be measured by measuring the potential difference between the first electrodes 21. The same applies to the second electrodes 22. Furthermore, if multiple electrodes are provided, a voltage can be applied to a wide range of the heart, whereby efficient defibrillation can be performed.

To the first electrodes 21, voltages of the same polarity (positive or negative) are preferably applied, and to the second electrodes 22, voltages of the same polarity (negative or positive) are preferably applied. For example, in the case of applying a biphasic DC voltage as shown in FIG. 2, the first electrodes 21 are negative and the second electrodes 22 are positive in the first half of current application, so that a current flows from the right atrium toward the coronary sinus, and in the latter half of the current application, the first electrodes 21 are positive and the second electrodes 22 are negative, so that a current flows from the coronary sinus toward the right atrium.

When the catheter 20 has the first electrodes 21, the second electrode 22 is preferably disposed closer to the proximal side than the most proximal first electrode 21. Due to such arrangement of the first electrode 21 and the second electrode 22, defibrillation can be efficiently performed.

As shown in FIGS. 1 and 3, it is preferable that a third electrode 23 for measuring the intracardiac potential be further provided between the first electrode 21 and the second electrode 22 in the longitudinal direction of the catheter 20. Due to the third electrode 23 being provided as described above, the intracardiac potential between the first electrode 21 and the second electrode 22 can also be measured. The third electrode 23 is preferably not connected to a power supply part 6. With this configuration, the third electrode 23 can be used as a dedicated electrode measuring the intracardiac potential.

As shown in FIGS. 1 and 3, it is preferable that a fourth electrode 24 for measuring the intracardiac potential be further provided closer to the proximal side than the second electrode 22 in the longitudinal direction of the catheter 20. Due to the fourth electrode 24 being provided as described above, the intracardiac potential on a point closer to the proximal side than the second electrode 22 can be measured. The fourth electrode 24 can be disposed at a position corresponding to, for example, the superior vena cava. The fourth electrode 24 is preferably not connected to the power supply part 6. With this configuration, the fourth electrode 24 can be used as a dedicated electrode measuring the intracardiac potential.

In the following, the first electrode 21, the second electrode 22, the third electrode 23, and the fourth electrode 24 may be collectively referred to as the "electrode", and each of the first electrode 21, the second electrode 22, the third electrode 23, and the fourth electrode 24 may be referred to as "each electrode".

The numbers of respective electrodes are not particularly limited, and the numbers of the respective electrodes may be the same or different from each other. Particularly, it is preferable that the number of the first electrodes 21 and the number of the second electrodes 22 be the same. This can easily make the first electrodes 21 and the second electrodes 22 have the same surface area. Due to the configuration in which the first electrodes 21 and the second electrodes 22 have the same surface area, and the first electrodes 21 and the second electrodes 22, the numbers of which are equal, are uniformly arranged, efficient defibrillation can be performed, and the measurement accuracy of intracardiac electrocardiogram can be increased.

The number of the third electrodes 23 is preferably less than or equal to the number of the first electrodes 21, and more preferably less than or equal to the number of the first electrodes 21 and less than or equal to the number of the second electrodes 22. When the number of the third electrodes 23 is set as described above, the intracardiac potential at each position of the heart can be appropriately measured. For example, the number of the first electrodes 21 and the number of the second electrodes 22 can be set to eight, and the number of the third electrodes 23 can be set to six.

The number of the fourth electrodes 24 is preferably equal to or less than the numbers of the first electrodes 21, the second electrodes 22, and the third electrodes 23. For example, the number of the first electrodes 21 and the number of the second electrodes 22 can be set to eight, the number of the third electrodes 23 can be set to six, and the number of the fourth electrodes 24 can be set to four. Due to the setting of the number of the fourth electrodes 24 as described above, the potential at the position corresponding to the superior vena cava can be appropriately measured.

It is preferable that each electrode be present in at least a half region of the outer circumference of the resin tube, and it is more preferable that each electrode be formed in a ring shape. When each electrode is formed in the manner described above, the contact area between each electrode and the heart increases, which facilitates the measurement of intracardiac potential and application of electrical stimulation.

When multiple electrodes are provided, the spacing between adjacent electrodes, that is, the distance between the distal end of one electrode and the proximal end of the other electrode that is located closer to the distal side than one electrode can be set to 1 mm or more and 10 mm or less, and more preferably set to 3 mm or more and 8 mm or less. Further, the width of each electrode can be set to, for example, 0.5 mm or more and 5 mm or less. The electrodes may have the same width or different widths. By setting the distance between the electrodes and the electrode width as described above, the intracardiac potential can be appropriately measured. In order to make the contact conditions with the cardiac muscle equal, it is preferable that the two electrodes measuring the potential have the same width or the same surface area. The electrode width indicates the length of each electrode in the longitudinal direction.

It is preferable that the distance between the most proximal electrode of the first electrodes 21 and the most distal electrode of the second electrodes 22 be longer than the distance between the first electrodes 21 and longer than the distance between the second electrodes 22. When the distance between the first electrode 21 and the second electrode 22 is set as described above, the electrodes are easily placed at predetermined positions of the heart on the basis of the distance. For example, the electrode arrangement and the distance between the electrodes may be set so that the first electrode 21 can be placed in the coronary sinus and the second electrode 22 can be placed in the right atrium. Here, the distance between the first electrodes 21 refers to the longest distance among the distances between two adjacent first electrodes 21. The same applies to the distance between the second electrodes 22.

Each electrode only needs to include a conductive material such as platinum or stainless steel, but preferably contains a radiopaque material such as platinum in order to easily recognize the position of the electrode under X-ray fluoroscopy.

As shown in FIG. 1, a distal tip 25 may be provided at the distal end part of the catheter 20. The distal tip 25 preferably has a tapered portion having an outer diameter which decreases toward the distal side. The distal tip 25 may be made of a conductive material. This allows the distal tip 25 to function as an electrode. Alternatively, the distal tip 25 may be made of a polymer material. Further, the hardness of the distal tip 25 may be set lower than the hardness of the resin tube in order to protect the internal tissues from contacting with the catheter 20.

An operation wire or a spring member for bending the distal side of the catheter 20 may be provided in the lumen of the resin tube. Specifically, it is preferable that the distal end part of the operation wire be fixed to the distal end part of the resin tube or the distal tip 25, and the proximal end part of the operation wire be fixed to a handle 26 described later.

A first lead wire 31 is connected to each electrode. Specifically, the inner peripheral surface of each electrode and one end part of the first lead wire 31 disposed in the lumen of the resin tube are joined to each other through a side hole provided in the outer peripheral surface of the resin tube. The other end part of the first lead wire 31 connected to the first electrode 21 or the second electrode 22 is preferably connected to a first connecting part 11 of the defibrillation power supply device 2 as described later. The other end part of the first lead wire 31 connected to the third electrode 23 or the fourth electrode 24 is preferably connected to a fourth connecting part 14 of the power supply device 2 as described later. The first lead wire 31 may include lead wires connected by a connecting member such as a connector. The same applies to a second lead wire 32 and a third lead wire 33 described later.

The handle 26 gripped by a user during operation of the catheter 20 may be provided on the proximal side of the resin tube. The shape of the handle 26 is not particularly limited, but it is preferable that the handle 26 be formed in a pyramidal shape whose outer diameter decreases toward the distal side in order to relieve stress concentration at the connection portion between the resin tube and the handle 26. The size of the handle 26 is not particularly limited as long as it is suitable for the user to hold with one hand. For example, the length thereof can be set to 5 cm or more and 20 cm or less, and the outermost diameter can be set to 1 cm or more and 5 cm or less. Examples of materials usable for the handle 26 include synthetic resin such as ABS or polycarbonate, and foamed plastic such as polyurethane foam. An opening may be provided in the proximal end part of the handle 26 (more preferably, the proximal end surface of the handle 26), and a part of the first lead wire 31 may extend from the opening, or the first lead wire 31 may be connected to a connector fixed to the opening.

The electrocardiograph 40 measures the intracardiac potential through various electrodes. A known device can be used as the electrocardiograph 40.

FIGS. 1 and 3 to 5 show the defibrillation power supply device 2 to be connected to the electrocardiograph 40 and the catheter 20 having electrodes. Hereinafter, the defibrillation power supply device may be simply referred to as "power supply device".

The present invention also includes the defibrillation power supply device 2 to be connected to the electrocardiograph 40 and the catheter 20 having electrodes. The defibrillation power supply device 2 includes a first connecting part 11 to be connected to electrodes provided on the distal side of the catheter 20, a second connecting part 12 to be connected to the electrocardiograph 40, the power supply part 6 for generating the voltage to be applied, and a changeover part 7 connected to the power supply part 6, the changeover part 7 switching between a first mode for measuring an intracardiac potential by the electrocardiograph 40 and a second mode for applying the voltage to the catheter 20 while the intracardiac potential is measured. The first connecting part 11 is connected to the power supply part 6 through the changeover part 7, and the first connecting part 11 is connected to the second connecting part 12 without a switching part. In the power supply device 2 according to the present invention, the first connecting part 11 is connected to the second connecting part 12 without the switching part, whereby a local potential at each electrode can be measured even during defibrillation.

The power supply device 2 is provided with an operation part 3 for performing various operations such as turning on or off the power supply device 2, setting an amount of energy to be applied, performing voltage charging, applying a voltage, and selecting an electrode to which a voltage is to be applied. As the operation part 3, known input means such as a button switch or a lever can be used. The operation part 3 is connected to a control part 4 described later, and an input signal from the operation part 3 is transmitted to the control part 4.

The power supply device 2 is provided with the control part 4 that controls the power supply part 6 and the changeover part 7 on the basis of an input signal from the operation part 3. The control part 4 is connected to a processing part 5, which has an output circuit for outputting a DC voltage from the power supply part 6 to the electrodes, through the changeover part 7. In the output circuit of the processing part 5, DC voltages having different polarities are applied to the first electrode 21 and the second electrode 22. The waveform to be applied may be biphasic with reversed polarity, or monophasic with constant polarity, but biphasic waveform is preferable, because it is considered that the biphasic waveform enables stimulation with less energy. The energy to be applied to the living body can be set to, for example, 1 J or more and 30 J or less.

The power supply part 6 is connected to the catheter 20 and generates a voltage to be applied. The power supply part 6 is provided with a power supply circuit for generating a DC voltage. The power supply circuit includes, for example, a booster circuit that boosts the DC voltage and a capacitor 19 charged with a voltage to be applied.

The power supply part 6 is connected with the changeover part 7 switching between a first mode for measuring an intracardiac potential and a second mode for applying a voltage to the catheter 20 while an intracardiac potential is measured. The first electrode 21 and the second electrode 22 are connected to the power supply part 6 through the changeover part 7. Therefore, when the first mode is selected by opening a switch constituting the changeover part 7 as shown in FIG. 3, the first electrode 21 and the second electrode 22 are insulated from the power supply part 6. Therefore, the intracardiac potential can be measured using the first electrode 21 and the second electrode 22 without performing defibrillation. Further, when the second mode is selected by closing the switch constituting the changeover part 7 as shown in FIG. 5, the first electrode 21 and the second electrode 22 are electrically connected to the power supply part 6. Therefore, a voltage can be applied to the heart.

The changeover part 7 preferably operates in conjunction with an input to the operation part 3. For example, it is preferable that the operation part 3 have a power button that activates the power supply device 2 and an application button that is a defibrillation switch, and the first mode be automatically selected when the power button is pressed, while the second mode be selected when the application button is pressed. It is preferable that the first mode be automatically selected after the application. The time in which the second mode is selected is preferably as short as possible. With this configuration, an electrocardiogram can be obtained with high accuracy. The operation part 3 preferably includes a charge button for charging the capacitor 19. It is preferable that the first mode be continued during charging, and the first mode be continued until just before the application button is pressed. The moment the defibrillation voltage is applied, the heart receives a large amount of energy, so that the intracardiac potential displayed on the electrocardiograph 40 is greatly disturbed. On the other hand, when the time in which the second mode is selected is as short as possible as described above, high-precision intracardiac electrocardiogram with no wave damping or rounding waveform can be continuously observed except at the moment when the intracardiac potential is significantly disturbed by application of the defibrillation voltage.

The first electrode 21 and the second electrode 22 are connected to the electrocardiograph 40 without the switching part. In other words, the switching part is not provided in the middle of an electric path connecting the first electrode 21 and the second electrode 22 to the electrocardiograph 40. Here, the switching part is a section for opening and closing the electric path and switching a direction in which a current flows. Therefore, the electric path from the first electrode 21 or the second electrode 22 to the electrocardiograph 40 is not opened or closed, or is not switched, and thus, the first electrode 21 and the second electrode 22 are constantly connected to the electrocardiograph 40. Consequently, according to the defibrillation catheter system 1 of the present invention, the intracardiac potential at each electrode can be measured even during defibrillation.

The first electrode 21 and the second electrode 22 are preferably connected to the electrocardiograph 40 without the changeover part 7. The reason is that, because the changeover part 7 switching between the first mode and the second mode is provided to connect or disconnect the first electrodes 21 to or from each other and to connect or disconnect the second electrodes 22 to or from each other, the changeover part 7 is included in the switching part in the present invention. The switching part is not provided in the electric path connecting the first electrode 21 and the electrocardiograph 40 and the electric path connecting the second electrode 22 and the electrocardiograph 40. Therefore, the first electrode 21 and the second electrode 22 are constantly connected to the electrocardiograph 40 regardless of whether the first mode or the second mode is selected. Therefore, the intracardiac potential can be measured by each electrode even during defibrillation.

More preferably, the first electrode 21 and the second electrode 22 are connected to the electrocardiograph 40 without any kinds of switching parts. With this configuration, the first electrode 21 and the second electrode 22 can be constantly connected to the electrocardiograph 40.

If an input unit of the electrocardiograph 40 is compatible with a defibrillation-proof applied part even when the second mode is selected by the changeover part 7, excessive current does not flow from the power supply part 6 toward the electrocardiograph 40. Therefore, the first electrode 21 and the second electrode 22 may be connected to the electrocardiograph 40 without the switching part. According to JIS T0601-1: 2017, Medical electrical equipment, Part 1: General requirements for basic safety and essential performance, 8.5.5.1 Defibrillation protection, the input of a defibrillation-proof applied part of medical equipment is required to withstand a discharge of 5 kV input through a resistance of 50Ω. The voltage to be applied by the defibrillation catheter system 1 is, for example, at a maximum of 600 V which is sufficiently smaller than 5 kV. Therefore, the electrocardiograph 40 can be sufficiently protected from overvoltage, also due to a resistance of 200Ω or less, more preferably a resistance of 50Ω or more and 200Ω or less being connected between the first electrode 21 and the electrocardiograph 40 and between the second electrode 22 and the electrocardiograph 40 as described later.

As shown in FIG. 6 a resistance 17 of 200Ω or less may be provided between the power supply part 6 and the electrocardiograph 40. If the resistance 17 is 200Ω or less, the intracardiac potential can be transmitted to the electrocardiograph 40 without rounding the waveform of the intracardiac potential acquired by the catheter 20. The resistance 17 provided between the power supply part 6 and the electrocardiograph 40 may be 150Ω or less, or 100Ω or less, and may be 50Ω or more, or 70Ω or more.

The changeover part 7 may have one or more switches. As shown in FIG. 3, the changeover part 7 preferably has first switches 7A connected in parallel with each other and second switches 7B connected in parallel with each other. In a case where the catheter 20 has a plurality of first electrodes 21 and a plurality of second electrodes 22, each of the first electrodes 21 is connected to the power supply part 6 through the corresponding one of the first switches 7A, and each of the second electrodes 22 is connected to the power supply part 6 through the corresponding one of the second switches 7B. That is, it is preferable that the first electrodes 21 and the second electrodes 22 be each connected to the power supply part 6 through different switches. As a result, multiple electrodes can be electrically separated, so that each electrode can independently acquire an intracardiac potential.

The first switches 7A and the second switches 7B are preferably of a multi-pole single-throw switch. If each switch is of a multi-pole single-throw switch, multiple switches can be activated in conjunction with one another by one operation, so that the accuracy of a timing at which a voltage is applied to each electrode can be enhanced.

As shown in FIG. 3, the first switches 7A and the second switches 7B may be of a single-pole single-throw switch. If each switch is of the single-pole single-throw switch, each switch can be operated individually, which makes it easy to apply a voltage to only a specific electrode.

The other end of the first lead wire 31 connected to the first electrode 21 or the second electrode 22 is connected to the first connecting part 11. Further, the first connecting part 11 and the changeover part 7 are connected through a fourth lead wire 34. Accordingly, the first electrode 21 and the second electrode 22 are connected to the power supply part 6, and thus a voltage can be applied. The first electrode 21 and the second electrode 22 may be connected to the power supply part 6 through different connecting members such as a connector.

In order to facilitate the connection between the power supply device 2 and the catheter 20, it is preferable that the first connecting part 11 have a recess, the other end of the first lead wire 31 be fixed to a first connector having a projection, and the projection be engageable with the recess.

The other end of the second lead wire 32 connected to an input terminal 41 of the electrocardiograph 40 corresponding to the first electrode 21 or the second electrode 22 is connected to the second connecting part 12. Further, the second connecting part 12 is connected to the fourth lead wire 34 through a fifth lead wire 35. No switching part is provided on the fourth lead wire 34 and the fifth lead wire 35. Accordingly, the first electrode 21 and the second electrode 22 are connected to the electrocardiograph 40 without the switching part, and therefore, the intracardiac potential can be measured through the first electrode 21 and the second electrode 22 even during defibrillation. Here, the fourth lead wire 34 and the fifth lead wire 35 may be a wiring material or may be a part of a wiring pattern provided on a printed board. It is preferable that the second connecting part 12 have a recess, the other end of the second lead wire 32 be fixed to a second connector having a projection, and the projection of the second connector be engageable with the recess in the second connecting part 12. This facilitates the connection between the power supply device 2 and the input terminal 41 of the electrocardiograph 40.

The power supply device 2 may include a third connecting part 13 that transmits the electrocardiographic waveform output from the electrocardiograph 40 to the control part 4. The third lead wire 33 connected to an output terminal 42 of the electrocardiograph 40 and the control part 4 are connected to the third connecting part 13. Thus, the electrocardiographic waveform output from the electrocardiograph 40 can be transmitted to the control part 4, so that the timing of applying the voltage can be controlled so as to be synchronized with the R wave during defibrillation. It is preferable that the third connecting part 13 have a recess, the other end of the third lead wire 33 be fixed to a third connector having a projection, and the projection of the third connector be engageable with the recess in the third connecting part 13. This facilitates connection between the power supply device 2 and the output terminal 42 of the electrocardiograph 40.

The power supply device 2 may have a fourth connecting part 14 and a fifth connecting part 15 that connect the electrocardiograph 40 to the third electrode 23 and the fourth electrode 24 which are electrodes dedicated to the measurement of the intracardiac potential. The other end of the first lead wire 31 connected to the third electrode 23 or the fourth electrode 24 is connected to the fourth connecting part 14. The other end of the second lead wire 32 connected to the input terminal 41 of the electrocardiograph 40 corresponding to the third electrode 23 or the fourth electrode 24 is connected to the fifth connecting part 15. The fourth connecting part 14 and the fifth connecting part 15 are connected through a sixth lead wire 36. Here, the sixth lead wire 36 may be a wiring material or a part of a wiring pattern provided on the printed board. For the same reason as the first connecting part 11 to the third connecting part 13, it is preferable that the fourth connecting part 14 and the fifth connecting part 15 have recesses, the projection of the first connector be engageable with the recess of the fourth connecting part 14, and the projection of the second connector be engageable with the recess of the fifth connecting part 15.

Examples of the recesses in the first to fifth connecting parts 11 to 15 include a known jack and receptacle, and examples of the projections formed on the first to third connectors include a pin terminal and a plug.

The power supply device 2 may have an electrode selection switch selecting from the first and second electrodes 21, 22 at least one electrode to which a voltage is applied. With this configuration, electrical stimulation can be applied only to a specific electrode. The position where the electrode selection switch is provided is not particularly limited. However, it is preferable that the electrode selection switch be connected to the power supply part 6, and it is more preferable that the electrode selection switch be provided in the output circuit of the processing part 5. The electrode selection switch may be provided separately from the switches (for example, the first switches 7A and the second switches 7B) constituting the changeover part 7, or at least one of the switches constituting the changeover part 7 may be the electrode selection switch.

As shown in FIG. 3, the power supply device 2 may be provided with a safety switch (safety switch 10). Due to this configuration, a fail-safe function that can prevent unintended application of voltage to the patient when, for example, the changeover part 7 fails can be provided to the power supply device. The safety switch 10 is preferably connected between the changeover part 7 and the power supply part 6, and more preferably connected between the processing part 5 and the changeover part 7. The number of safety switches 10 is not particularly limited, but it is preferable that at least one safety switch 10 be provided for the first electrodes 21 and at least one safety switch 10 be provided for the second electrodes 22. Note that FIG. 3 shows an example in which one safety switch 10 is connected to the processing part 5 and the first switches 7A, and another safety switch 10 is connected to the processing part 5 and the second switches 7B.

The power supply device 2 may be provided with a protection circuit that absorbs a high voltage generated when the switch is cut off. This can prevent damage to each switch.

As shown in FIG. 6, the power supply device 2 may be provided with an overvoltage protection circuit 18 for protecting the electrocardiograph 40 from overvoltage between the power supply part 6 and the electrocardiograph 40. This configuration can prevent the electrocardiograph 40 from being damaged by the application of overvoltage.

As shown in FIGS. 3 to 5, it is preferable that an impedance measuring circuit 8 for measuring an impedance between the first electrode 21 and the second electrode 22 be connected between the first electrode 21 and the second electrode 22, the first electrode 21 be connected to the impedance measuring circuit 8 through a third switch 9A, and the second electrode 22 be connected to the impedance measuring circuit 8 through a fourth switch 9B. With this configuration, the impedance between the first electrode 21 and the second electrode 22 can be measured, whereby a waveform to be applied suitable for the patient can be set. FIGS. 3 to 5 show an example in which one third switch 9A is provided for each of the first electrodes 21, and one fourth switch 9B is provided for each of the second electrodes 22.

Similar to the first switches 7A and the second switches 7B, the electrode selection switch, the safety switch 10, the third switch 9A, and the fourth switch 9B may be of a single-pole single-throw switch or a multi-pole single-throw switch.

Second Embodiment

The power supply parts 6 described in the first embodiment may be provided. For example, it is preferable that a catheter system include, as the power supply part 6, at least a first power supply part and a second power supply part, and as the changeover part 7, at least a first changeover part and a second changeover part, the catheter 20 have, as the first electrode 21, at least a 1-1 electrode and a 1-2 electrode, and as the second electrode 22, at least a 2-1 electrode and a 2-2 electrode, the first power supply part be connected to the first changeover part, the second power supply part be connected to the second changeover part, the 1-1 electrode and the 2-1 electrode be connected to the first power supply part through the first changeover part, the 1-2 electrode and the 2-2 electrode be connected to the second power supply part through the second changeover part, and the 1-1 electrode, the 1-2 electrode, the 2-1 electrode, and the 2-2 electrode be connected to the electrocardiograph 40 without a switching part. Due to the configuration in which the power supply parts 6 are provided as described above, a capacitor having relatively small capacitance can be used as a capacitor built in each power supply part 6. Further, since the capacitance of the capacitor is reduced, a charging time of energy to be delivered can be decreased, and the device can be downsized.

The defibrillation catheter system 1 according to the second embodiment can be configured such that one operation part 3 and one single control part 4 are provided, the power supply parts 6 are connected to the control part 4, and processing parts 5 and the changeover parts 7 are connected to the respective power supply parts 6.

It is preferable that a synchronization circuit that synchronizes timings for applying a voltage to the 1-1 electrode, the 2-1 electrode, the 1-2 electrode, and the 2-2 electrode be connected to the first power supply part and the second power supply part. Due to the synchronization circuit being provided as described above, even if voltages are generated by different power supply parts, timings for applying the voltages to the respective electrodes can be synchronized, which makes it easy to complete the voltage application within the absolute refractory period.

Preferably, two or more electrodes, more preferably, four or more electrodes, are connected to each power supply part 6. Specifically, it is preferable that a plurality of first electrodes 21 (for example, 1-1 electrode, 1-3 electrode) and a plurality of second electrodes 22 (for example, 2-1 electrode, 2-3 electrode) be connected to the first power supply part through the first changeover part, and another plurality of the first electrodes 21 (for example, 1-2 electrode, 1-4 electrode) and another plurality of the second electrodes 22 (for example, 2-2 electrode, 2-4 electrode) be connected to the second power supply part through the second changeover part. In that case, it is preferable that the first changeover part include a 1-1 switch connected to the 1-1 electrode, a 1-3 switch connected to the 1-3 electrode, a 2-1 switch connected to the 2-1 electrode, and a 2-3 switch connected to the 2-3 electrode, and the second changeover part include a 1-2 switch connected to the 1-2 electrode, a 1-4 switch connected to the 1-4 electrode, a 2-2 switch connected to the 2-2 electrode, and a 2-4 switch connected to the 2-4 electrode. Due to each electrode having a switch as described above, each electrode can independently acquire an intracardiac potential, or a voltage can be independently applied to each electrode. The numbers of electrodes connected to the respective power supply parts 6 may be the same or different, but it is preferable that they be the same in order to facilitate control.

The number of power supply parts 6 can be set according to the number of first electrodes 21 and the number of second electrodes 22, but preferably, three or more power supply parts 6 including the first power supply part and the second power supply part are provided. As the number of power supply parts 6 is increased, the capacitance of the capacitor can be reduced more, so that the charging time of energy to be delivered can be decreased, and the device can be downsized. However, in order to prevent the power supply device 2 from becoming complicated, the number of power supply parts 6 is preferably ten or less, and more preferably eight or less.

Hereinafter, an operation for measuring an intracardiac potential and applying a voltage using the defibrillation catheter system 1 according to the first embodiment will be described. Note that the configurations of the defibrillation catheter system 1 and the defibrillation power supply device 2 are not limited to those in the present embodiment.

(Step 1: Measurement of Intracardiac Potential)

As shown in FIGS. 1 and 3, the power supply device 2, the catheter 20, and the electrocardiograph 40 are connected. The catheter 20 is inserted into the cardiac cavity, and the electrodes are placed at the desired locations of the heart.

As shown in FIG. 3, the first mode for measuring the intracardiac potential is set by the changeover part 7. For example, the first mode can be set by opening all the switches constituting the changeover part 7. The first electrodes 21 and the second electrodes 22 are connected to the electrocardiograph 40 through the first connecting part 11 and the second connecting part 12. The potential measured by each electrode is transmitted to the electrocardiograph 40, and the intracardiac electrocardiogram is displayed in the electrocardiograph 40 or a display unit provided separately from the electrocardiograph 40.

It is preferable that the changeover part 7 be in the first mode in the initial state when the power supply of the power supply device 2 is turned on. Thus, the intracardiac electrocardiographic measurement can be started when the power supply is turned on, so that an abnormality can be detected early.

(Step 2: Setting Amount of Energy to be Applied)

An amount of energy to be applied is set using the operation part 3. For example, an arbitrary amount of energy from 1 J to 30 J can be set.

(Step 3: Charging of Energy to be Applied and Measurement of Impedance)

The defibrillation power supply device 2 has a capacitor 19 and the changeover part 7 switching between the first mode for measuring an intracardiac potential by the electrocardiograph 40 and the second mode for applying a voltage to the catheter 20 while an intracardiac potential is measured by the electrocardiograph 40. When the charge button of the operation part 3 is operated, the power supply part 6 charges the capacitor 19 built in the power supply part 6 with a voltage. That is, the method for controlling the power supply device 2 which is connected to the electrocardiograph 40 and the catheter 20 having electrodes to generate a voltage to be applied according to the present invention preferably includes a charging step for charging the capacitor 19 with the voltage to be applied while the intracardiac potential is measured by the electrocardiograph 40 when the changeover part 7 is in the first mode. Accordingly, the intracardiac potential having no waveform rounding can be measured independently by each electrode even while the capacitor 19 is being charged. When charging of a voltage corresponding to the amount of energy to be applied set in step 2 is completed, the voltage is maintained. It is preferable that, when the charge button is operated, the impedance between the first electrodes 21 and the second electrodes 22 be measured in parallel with the voltage charging. Specifically, as shown in FIG. 4, the changeover part 7 closes all the switches 9A and 9B connected to the impedance measuring circuit 8 in the first mode. As a result, the value of the bioelectrical impedance before current application can be acquired, so that the waveform to be applied can be appropriately set according to the bioelectrical impedance of the patient. The AC voltage applied for measuring the impedance has a frequency and a voltage value enough to calculate the impedance, and the AC voltage only has to be sufficiently lower than the voltage to be applied during defibrillation. During the acquisition of the impedance value, the switches 9A and 9B are closed, and the first electrodes 21 and the second electrodes 22 are connected to each other, so that the intracardiac potential waveform obtained by averaging the intracardiac potentials at the respective sites is obtained. Therefore, it is preferable that the measurement time of the impedance be shorter. Preferably, the measurement time is several tens to several hundred of milliseconds. In addition, after the impedance measurement, the third switch 9A and the fourth switch 9B are opened.

In the system 1 according to the present invention, the first electrodes 21 and the second electrodes 22 are connected to the electrocardiograph 40 without a switching part. Therefore, even during charging of energy to be delivered and while the charged voltage is maintained, a local potential at each electrode can be acquired.

(Step 4: Defibrillation)

When the application button of the operation part 3 is operated, the defibrillation voltage is applied to the patient in synchronization with the R wave of the electrocardiographic waveform input to the third connecting part 13 from the electrocardiograph 40. Specifically, the changeover part 7 is switched to the second mode by closing all switches of the changeover part 7 including the first switches 7A and the second switches 7B, and the control part 4 selects the waveform to be applied and the energy to be delivered determined in step 3. The power supply part 6 discharges the capacitor 19, and the processing part 5 applies a voltage to each electrode so as to generate a biphasic waveform based on the information from the control part 4. The voltage is applied in the absolute refractory period in order to prevent that ventricular fibrillation is caused due to the response of the ventricular muscles. The voltage only has to be applied so as to be synchronized with the R wave of the electrocardiographic waveform from the electrocardiograph 40. Immediately after the voltage application is completed, all the switches of the changeover part 7 including the first switches 7A and the second switches 7B are opened. The first electrodes 21 and the second electrodes 22 are connected to the electrocardiograph 40 without the switching part. Therefore, the local potentials at the first electrodes 21 and the second electrodes 22 can be continuously measured even during defibrillation, whereby the response of the heart before and after the defibrillation can be observed early.

This application claims the benefit of the priority date of Japanese patent application No. 2018-20529 filed on Feb. 7, 2018. All of the contents of the Japanese patent application No. 2018-20529 filed on Feb. 7, 2018 are incorporated by reference herein.

REFERENCE SIGNS LIST

1: Defibrillation catheter system
2: Defibrillation power supply device (Power supply device)
3: Operation part
4: Control part
5: Processing part
6: Power supply part
7: Changeover part
7A: First switch
7B: Second switch
8: Impedance measuring circuit
9A: Third switch
9B: Fourth switch
10: Safety switch
11: First connecting part
12: Second connecting part
13: Third connecting part
14: Fourth connecting part
15: Fifth connecting part
17: Resistance
18: Overvoltage protection circuit
19: Capacitor
20: Catheter
21: First electrode
22: Second electrode
23: Third electrode
24: Fourth electrode
25: Distal tip
26: Handle
31: First lead wire
32: Second lead wire
33: Third lead wire
34: Fourth lead wire
35: Fifth lead wire
36: Sixth lead wire
40: Electrocardiograph
41: Input terminal of the electrocardiograph
42: Output terminal of the electrocardiograph

The invention claimed is:

1. A defibrillation catheter system comprising:
a catheter extending in a longitudinal direction from a distal end to a proximal end;
a power supply part for generating a voltage to be applied to the catheter, the power supply part connected to the catheter;
an electrocardiograph for measuring an intracardiac potential;
a first electrode provided on a distal side of the catheter;
a second electrode provided on the distal side of the catheter and disposed closer to a proximal side than the first electrode; and
a changeover part connected to the power supply part, the changeover part switching between a first mode for measuring the intracardiac potential by the first electrode and the second electrode, and a second mode for applying the voltage to the first electrode and the second electrode of the catheter while the intracardiac potential is measured by the first electrode and the second electrode, wherein
the first electrode and the second electrode are connected to i) the power supply part through the changeover part and ii) the electrocardiograph without a switching part so that the intracardiac potential can be measured while the changeover part is in position of the second mode to apply the voltage to the first electrode and the second electrode of the catheter.

2. The system according to claim 1, wherein
the changeover part has first switches connected in parallel with each other and second switches connected in parallel with each other,
the catheter has a plurality of the first electrodes and a plurality of the second electrodes,
each of the first electrodes is connected to the power supply part through a corresponding one of the first switches, and
each of the second electrodes is connected to the power supply part through a corresponding one of the second switches.

3. The system according to claim 2, wherein
the first switches and the second switches are of a multi-pole single-throw switch.

4. The system according to claim 2, further comprising
a third switch connected to the first electrode, and
a fourth switch connected to the second electrode, wherein
the third and fourth switches, the first electrode, and the second electrode are configured to measure an impedance between the first electrode and the second electrode.

5. The system according to claim 1, further comprising
an electrode selection switch selecting from the first and second electrodes at least one electrode to which a voltage is applied, the electrode selection switch being connected to the power supply part.

6. The system according to claim 1, further comprising
a resistance of 200Ω or less, the resistance being provided between the power supply part and the electrocardiograph.

7. The system according to claim 1, wherein
the electrocardiograph and the power supply part are configured so that the electrocardiograph is protected from an overvoltage.

8. The system according to claim 1, further comprising a third electrode for measuring the intracardiac potential, the third electrode provided between the first electrode and the second electrode in the longitudinal direction of the catheter.

9. The system according to claim 1, further comprising a fourth electrode for measuring the intracardiac potential, the fourth electrode provided closer to the proximal side than the second electrode in the longitudinal direction of the catheter.

10. The system according to claim 1, wherein
the system includes, as the power supply part, at least a first power supply part and a second power supply part, and as the changeover part, at least a first changeover part and a second changeover part,
the catheter has, as the first electrode, at least a 1-1 electrode and a 1-2 electrode, and as the second electrode, at least a 2-1 electrode and a 2-2 electrode,
the first power supply part is connected to the first changeover part,
the second power supply part is connected to the second changeover part,
the 1-1 electrode and the 2-1 electrode are connected to the first power supply part through the first changeover part,
the 1-2 electrode and the 2-2 electrode are connected to the second power supply part through the second changeover part, and
the 1-1 electrode, the 1-2 electrode, the 2-1 electrode, and the 2-2 electrode are connected to the electrocardiograph without a switching part.

11. A defibrillation power supply device to be connected to an electrocardiograph and a catheter having electrodes, the defibrillation power supply device comprising:
a first connecting part to be connected to electrodes provided on a distal side of the catheter;
a second connecting part to be connected to the electrocardiograph;
a power supply part for generating the voltage to be applied; and
a changeover part connected to the power supply part, the changeover part switching between a first mode for measuring an intracardiac potential by the electrocardiograph and a second mode for applying the voltage to the catheter while the intracardiac potential is measured, wherein
the first connecting part is connected to the power supply part through the changeover part,
the first connecting part is connected to the second connecting part without a switching part,
the first connecting part and electrodes are connected through a first lead wire,
the second connecting part and the electrocardiograph are connected through a second lead wire,
the defibrillation power supply device and the electrocardiograph are connected through a third lead wire,
the first connecting part and the changeover part are connected through a fourth lead wire,
the second connecting part is connected to the fourth lead wire through a fifth lead wire, and
the fourth lead wire and the fifth lead wire are directly connected.

* * * * *